US010428177B2

(12) United States Patent
Sullivan et al.

(10) Patent No.: US 10,428,177 B2
(45) Date of Patent: Oct. 1, 2019

(54) WATER ABSORBING OR WATER SOLUBLE POLYMERS, INTERMEDIATE COMPOUNDS, AND METHODS THEREOF

(71) Applicant: Sirrus, Inc., Loveland, OH (US)

(72) Inventors: Jeffrey M. Sullivan, Goshen, OH (US); Ami Doshi, Loveland, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/610,854

(22) Filed: Jun. 1, 2017

(65) Prior Publication Data

US 2017/0349701 A1 Dec. 7, 2017

Related U.S. Application Data

(63) Continuation-in-part of application No. 15/592,829, filed on May 11, 2017, now Pat. No. 10,196,481, which is a continuation-in-part of application No. 15/472,379, filed on Mar. 29, 2017, now Pat. No. 10,087,283, which is a continuation of application No. 15/437,164, filed on Feb. 20, 2017, now Pat. No. 9,745,413, which is a continuation of application No.
(Continued)

(51) Int. Cl.
| | |
|---|---|
| *C08F 267/06* | (2006.01) |
| *C08F 122/20* | (2006.01) |
| *C08G 63/52* | (2006.01) |
| *B32B 27/36* | (2006.01) |
| *C12P 7/62* | (2006.01) |
| *C09D 151/08* | (2006.01) |

(52) U.S. Cl.
CPC .............. *C08G 63/52* (2013.01); *B32B 27/36* (2013.01); *C09D 151/08* (2013.01); *C12P 7/625* (2013.01)

(58) Field of Classification Search
CPC .. C08F 122/02; C08F 122/105; C08F 122/20; C08F 267/02; C08F 267/06
See application file for complete search history.

(56) References Cited

U.S. PATENT DOCUMENTS

| | | |
|---|---|---|
| 2,212,506 A | 8/1940 | Bachman |
| 2,245,567 A | 6/1941 | Brant et al. |

(Continued)

FOREIGN PATENT DOCUMENTS

| | | |
|---|---|---|
| CN | 102901754 A | 1/2013 |
| DE | 19508049 A1 | 9/1996 |

(Continued)

OTHER PUBLICATIONS

US 5,416,927 A, 05/1995, Spangrud (withdrawn)
(Continued)

*Primary Examiner* — Vu A Nguyen
(74) *Attorney, Agent, or Firm* — Young Basile Hanlon & MacFarlane, P.C.

(57) ABSTRACT

Disclosed are graft copolymers, compositions including graft copolymers, intermediate materials, and related methods, where the graft copolymer includes a first polymer component including a 1,1-disubstituted-1-alkene compound (preferably a methylene malonate compound) and is grafted to a second component. The resulting graft copolymer may be hydrophilic or water soluble. The second component preferably is a hydrophilic component.

20 Claims, 2 Drawing Sheets

Full scale H-NMR of transesterification of DEMM with PEG 300. Formation of new species can be confirmed in the 6.5 ppm methylene (double bond) region.

Integration of the two species seen in the 6.5 ppm region of the spectrum in 1A confirms the amount of transesterified species is about 35% (with about 65 wt.% residual DEMM).

Related U.S. Application Data

15/234,191, filed on Aug. 11, 2016, now Pat. No. 9,617,377.

(60) Provisional application No. 62/452,543, filed on Jan. 31, 2017, provisional application No. 62/421,754, filed on Nov. 14, 2016, provisional application No. 62/345,334, filed on Jun. 3, 2016.

(56) References Cited

U.S. PATENT DOCUMENTS

| | | |
|---|---|---|
| 2,277,479 A | 3/1942 | D'Aiello |
| 2,313,501 A | 3/1943 | Bachman |
| 2,330,033 A | 9/1943 | D'Aiello |
| 2,403,791 A | 7/1946 | D'Aiello |
| 3,042,710 A | 7/1962 | Dickstein et al. |
| 3,197,318 A | 7/1965 | Halpern et al. |
| 3,203,915 A | 8/1965 | D'Aiello |
| 3,221,745 A | 12/1965 | Coover |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender et al. |
| 3,936,486 A | 2/1976 | Egger et al. |
| 3,940,362 A | 2/1976 | Overhults |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Ami et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flaningam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,288,619 A | 2/1994 | Brown et al. |
| 5,292,937 A | 3/1994 | Manning et al. |
| 5,312,864 A | 5/1994 | Wenz et al. |
| 5,328,687 A | 7/1994 | Leung et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 10/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,238,896 B1 | 5/2001 | Ozaki et al. |
| 6,245,933 B1 | 6/2001 | Malofsky et al. |
| 6,255,038 B1 | 7/2001 | Hobbs |
| 6,284,915 B2 | 9/2001 | Hirase et al. |
| 6,291,703 B1 | 9/2001 | Schaertl, Jr. et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote et al. |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |

(56) References Cited

U.S. PATENT DOCUMENTS

| | | | |
|---|---|---|---|
| 6,673,957 B2 | 1/2004 | Bartek et al. | |
| 6,699,928 B2 | 3/2004 | Cobbley et al. | |
| 6,716,355 B1 | 4/2004 | Hanemaaijer et al. | |
| 6,750,298 B1* | 6/2004 | Bru-Magniez | B01F 17/0028 516/77 |
| 6,794,365 B2 | 9/2004 | Al-Obeidi et al. | |
| 6,841,064 B1 | 1/2005 | Weiss et al. | |
| 6,936,140 B2 | 8/2005 | Paxton et al. | |
| 7,070,675 B2 | 7/2006 | Schmidt et al. | |
| 7,109,369 B2 | 9/2006 | Nose et al. | |
| 7,208,621 B2 | 4/2007 | Nose et al. | |
| 7,226,957 B1 | 6/2007 | Scranton et al. | |
| 7,305,850 B2 | 12/2007 | Tonkovich et al. | |
| 7,553,989 B2 | 6/2009 | Sawabe et al. | |
| 7,603,889 B2 | 10/2009 | Cypes et al. | |
| 7,610,775 B2 | 11/2009 | Tonkovich et al. | |
| 7,649,108 B2 | 1/2010 | Schal et al. | |
| 7,659,423 B1 | 2/2010 | McArdle | |
| 7,663,000 B2 | 2/2010 | Dekkers et al. | |
| 7,771,567 B2 | 8/2010 | Rives et al. | |
| 7,829,738 B1 | 11/2010 | Brammer, Jr. et al. | |
| 7,900,558 B2 | 3/2011 | Yokoi | |
| 7,972,822 B2 | 7/2011 | Gross et al. | |
| 8,425,999 B2 | 4/2013 | McArdle et al. | |
| 8,609,885 B2 | 12/2013 | Malofsky et al. | |
| 8,884,051 B2 | 11/2014 | Malofsky et al. | |
| 9,108,914 B1 | 8/2015 | Malofsky et al. | |
| 9,181,365 B2 | 11/2015 | Malofsky et al. | |
| 9,217,098 B1 | 12/2015 | Stevenson et al. | |
| 9,221,739 B2 | 12/2015 | Malofsky et al. | |
| 9,234,107 B2 | 1/2016 | Malofsky et al. | |
| 9,334,430 A1 | 5/2016 | Stevenson et al. | |
| 9,416,091 B1 | 8/2016 | Sullivan et al. | |
| 9,429,265 B2 | 8/2016 | Onishi et al. | |
| 9,481,640 B2 | 11/2016 | McArdle et al. | |
| 2001/0005572 A1 | 6/2001 | Lobo et al. | |
| 2001/0034300 A1 | 10/2001 | Yurugi et al. | |
| 2002/0035231 A1 | 3/2002 | Whitehouse et al. | |
| 2002/0143128 A1 | 10/2002 | Cabioch et al. | |
| 2002/0151629 A1 | 10/2002 | Buffkin et al. | |
| 2003/0096069 A1 | 5/2003 | D'Alessio | |
| 2003/0199655 A1 | 10/2003 | Yurugi et al. | |
| 2004/0076601 A1 | 4/2004 | Bru-Magniez et al. | |
| 2004/0082043 A1 | 4/2004 | Yadav et al. | |
| 2004/0220060 A1 | 11/2004 | Bartley et al. | |
| 2006/0167267 A1 | 7/2006 | Chorghade et al. | |
| 2006/0211809 A1 | 9/2006 | Kodemura et al. | |
| 2007/0043145 A1 | 2/2007 | Beck et al. | |
| 2007/0049655 A1 | 3/2007 | Yoshimune et al. | |
| 2007/0092483 A1 | 4/2007 | Pollock | |
| 2007/0120630 A1 | 5/2007 | Huang et al. | |
| 2007/0238872 A1 | 10/2007 | Sabesan | |
| 2008/0131618 A1 | 6/2008 | Nakamura et al. | |
| 2008/0160305 A1 | 7/2008 | Warren et al. | |
| 2008/0187655 A1 | 8/2008 | Markle et al. | |
| 2008/0227919 A9 | 9/2008 | Li et al. | |
| 2008/0241485 A1 | 10/2008 | Shimohara et al. | |
| 2008/0286333 A1 | 11/2008 | Kangas et al. | |
| 2009/0203861 A1 | 8/2009 | Lee et al. | |
| 2009/0206861 A1 | 8/2009 | Shiraishi et al. | |
| 2009/0263604 A1 | 10/2009 | Arai et al. | |
| 2010/0016508 A1 | 1/2010 | Sasagawa et al. | |
| 2010/0256720 A1 | 10/2010 | Overstreet et al. | |
| 2010/0286433 A1 | 11/2010 | Malofsky et al. | |
| 2010/0286438 A1 | 11/2010 | Malofsky et al. | |
| 2011/0015406 A1 | 1/2011 | Umetani et al. | |
| 2011/0024392 A1 | 2/2011 | Sato et al. | |
| 2011/0164322 A1 | 7/2011 | Morozumi et al. | |
| 2011/0245522 A1 | 10/2011 | Wu et al. | |
| 2012/0083523 A1 | 4/2012 | Richard et al. | |
| 2012/0136130 A1 | 5/2012 | Takashima et al. | |
| 2012/0203021 A1 | 8/2012 | Friese et al. | |
| 2013/0019520 A1 | 1/2013 | Sello et al. | |
| 2013/0281580 A1 | 10/2013 | Malofsky et al. | |
| 2013/0303719 A1 | 11/2013 | Malofsky et al. | |
| 2013/0324754 A1 | 12/2013 | Bredsguard et al. | |
| 2014/0017741 A1 | 1/2014 | Nielsen et al. | |
| 2014/0058031 A1 | 2/2014 | Overbeek et al. | |
| 2014/0248485 A1 | 9/2014 | Malofsky et al. | |
| 2014/0275400 A1 | 9/2014 | Chen et al. | |
| 2014/0288230 A1 | 9/2014 | Malofsky et al. | |
| 2014/0329980 A1 | 11/2014 | Malofsky et al. | |
| 2015/0056879 A1 | 2/2015 | Malofsky et al. | |
| 2015/0073110 A1 | 3/2015 | Malofsky et al. | |
| 2015/0104660 A1 | 4/2015 | Malofsky et al. | |
| 2015/0148480 A1 | 5/2015 | Ellison et al. | |
| 2015/0210894 A1 | 7/2015 | Malofsky et al. | |
| 2015/0303122 A1 | 10/2015 | Malofsky et al. | |
| 2015/0361283 A1 | 12/2015 | Malofsky et al. | |
| 2016/0068616 A1 | 3/2016 | Palsule et al. | |
| 2016/0177349 A1 | 6/2016 | Addy et al. | |
| 2016/0221922 A1 | 8/2016 | Sullivan et al. | |

FOREIGN PATENT DOCUMENTS

| | | | |
|---|---|---|---|
| EP | 2768917 | A2 | 8/2014 |
| FR | 2788516 | A1 | 7/2000 |
| GB | 432628 | A | 7/1935 |
| GB | 965676 | A | 8/1964 |
| GB | 975733 | A | 11/1964 |
| GB | 1048906 | A | 11/1966 |
| JP | H02281013 | A | 11/1990 |
| JP | H08231564 | A | 9/1996 |
| JP | 200019936 | A | 1/2000 |
| JP | 2003201397 | A | 7/2003 |
| JP | 2008174494 | A | 7/2008 |
| WO | 1999046619 | A1 | 9/1999 |
| WO | 1999055394 | A1 | 11/1999 |
| WO | 2007120630 | A2 | 10/2007 |
| WO | 2010091975 | A1 | 8/2010 |
| WO | 2010129068 | A1 | 11/2010 |
| WO | 2011059104 | A1 | 5/2011 |
| WO | 2011161045 | A1 | 12/2011 |
| WO | 2012054616 | A2 | 4/2012 |
| WO | 2012054633 | A2 | 4/2012 |
| WO | 2013/059473 | A2 | 4/2013 |
| WO | 2013066629 | A1 | 5/2013 |
| WO | 2013149165 | A1 | 10/2013 |
| WO | 2013149168 | A1 | 10/2013 |
| WO | 2013149173 | A1 | 10/2013 |
| WO | 2013171302 | A1 | 11/2013 |

OTHER PUBLICATIONS

International Search Report and Written Opinion for International Application No. PCT/US2017/034501 dated Jul. 19, 2017.

March, Advanced Organic Chemistry, 2d Ed, section 0-25 pp. 365-367, 1977 McGraw Hill, New York, New York.

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.

McNab, Kirk-Othmer Encyclopedia of chemical Technology, Pyrolysis, Flash Vacuum, 2009, John Wiley & Sons, Inc., pp. 1-26.

Bock, "Diethyl bis (hydroxymethyl) malonate" Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

(56) References Cited

OTHER PUBLICATIONS

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

T. Doi et al.: "Synthesis of Dimethyl gloiosiphne a by Way of Palladium-Catalyzed Domino Cyclization," T. Ora <http://T.Ora>. Chem., (2007), vol. 72, pp. 3667-3671.

H. Jung et al,: "New and General Methods for the Synthesis of Arylmethylene Bis(3-Hydroxy-2-Cyclohexene-1-0nes) and Xanthenediones by EDDA and In(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,— (1998), vol. 39, No. I, pp. 173-181.

Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.

P, Ballesteros et al.: "D 1-tert-Butyl Methylenemalonate [Propanedioic Acid, Methylene-, bis( 1,1-dimethylethyl)ester]," Organic Syntheses. Coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes; via the Knoevenaqel Condensation," Tetrahedron Letters, (2002), vol. 43, pp. 1127-1130.

P. Ballesteros et al.: "Synthesis of Di-tert-butyl Methylenemalonate, a Sterically Hindered 1,1-Dicarbonyl Alkene," J. Ora <htto://J.Ora>. Chem, (1983), vol. 48, pp. 3603-3605.

M. Matziari et al. Active Methylene Phosphinic Peptides: A new Diversification Approach Organic Letters 2006 vol. 8, No. 11 pp. 2317-2319 May 5, 2006.

Zaragoza Dorwald, Side Reactions in Organic Synthesis, 2005, Wiley-VCH Verlag GmbH & Co., KgaA, Weinheim, Preface. p. IX.

K. Okamura and T. Date, A Facile Conversion of Ethoxydihydropyrans to 4-Cyanoethylisoxazoles, J. Heterocyclic Chem. 33, 383 (1996).

Yamauchi et al.; "Reactivity of 2-methylene-1, 3-dicarbonyl compounds: catalytic enantioselective Diels-Alder reaction"; Tetrahedron: Asymetry 12, (2001), 3113-3118.

Cristoph Schotes et al. "Cu(I)- and C(II)-Catalyzed Cyclo- and Michael Addition Reactions of Unsaturated [beta]-Ketoesters" The Journal of Organic Chemistry, vol. 76, No. 14 dated Jul. 15, 2011 p. 5862-5866.

Alejandro Bugarin et al. "Efficient direct [alpha]-methylenation of carbonyls mediated by dissopropylammonium trifluoroacetate", Chemical Communications, vol. 46, No. 10 dated Jan. 25, 2010.

H. Hoffman et al. "Preparation and Selected Reaction of tery-Butyl 2-Methylene-3-oxoalkanoates" Chem. Ber., vol. 124 dated Jan. 1, 1991, pp. 2475-2480.

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jan. 1, 2001, pp. 1638-1639.

Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.

Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.

P. Breton et al., "New Poly(Methylidudene Malonate 2.1.2) Nanoparticles: Recent Developments", Targeting of Drugs 4, NATO ASI Series, vol. 273, pp. 161-172, 1994.

Limouzin et al., "Anionic Polymerization of n-Butyl Cyanoacrylate in Emulsion and Miniemulsion" Macromolecules, vol. 36, 2003, pp. 667-674.

Morrison and Boyd, Organic Chemistry, 4th Ed, pp. 831 and 836-838, 1983 Allyn Bacon, Inc. Boston, Massachusetts.

Otera et al, "Esterification: Methods, Reactions, & Applications" "Esterification of Sludge Palm Oil Using Trifluromethanesulfonic Acid for preparation of Biodiesel Fuel" Korean Journal of Chemical Engineering, Jun. 2013, vol. 30, Issue 6, pp. 1229-1234.

Thimmaraju et al.,"Transsesterification of diethyl malonate with Benzyl Alcohol Catalyzed by Modified Zirconia: Kinetic Study", Journal of Molecular Catalysis A: Chemical, vol. 391, Sep. 2014, p. 55-65.

Olah et al, "Superelectrophilic Solvation," Accounts of Chemical Research, Apr. 2004, vol. 37, No. 4.

Kütt et al, "Equilibrium Acidities of Superacids," Journal of Organic Chemistry, vol. 76, No. 2, 2011, pp. 391-395, published on the web Dec. 17, 2010.

McCoy, M. "A New Way to Stick" Chemical & Engineering News, vol. 92, Issue 26, Jun. 30, 2014, pp. 17-18, paragraph [2].

Eckert et al., "Prediction of acidity in acetonitrile solution with COSMO-RS," Journal of Computational Chemistry 30(5), 2009, 799-810.

* cited by examiner

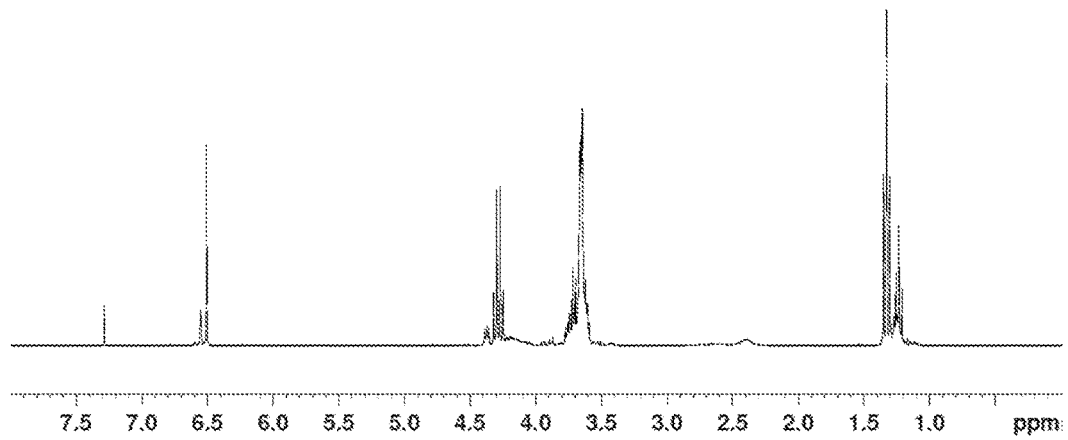
FIG. 1A: Full scale H-NMR of transesterification of DEMM with PEG 300. Formation of new species can be confirmed in the 6.5 ppm methylene (double bond) region.
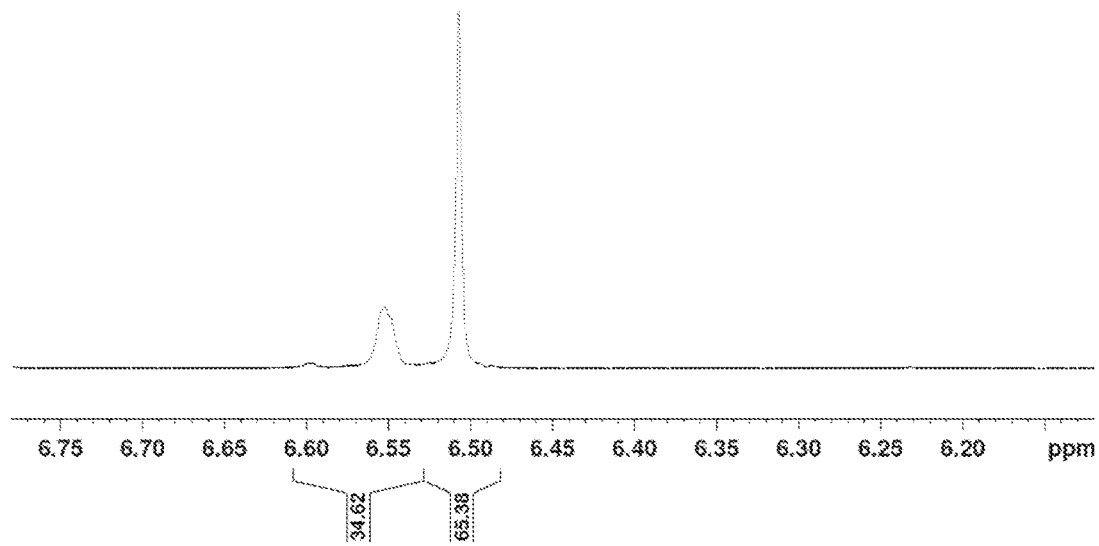
FIG. 1B: Integration of the two species seen in the 6.5 ppm region of the spectrum in 1A confirms the amount of transesterified species is about 35% (with about 65 wt.% residual DEMM).

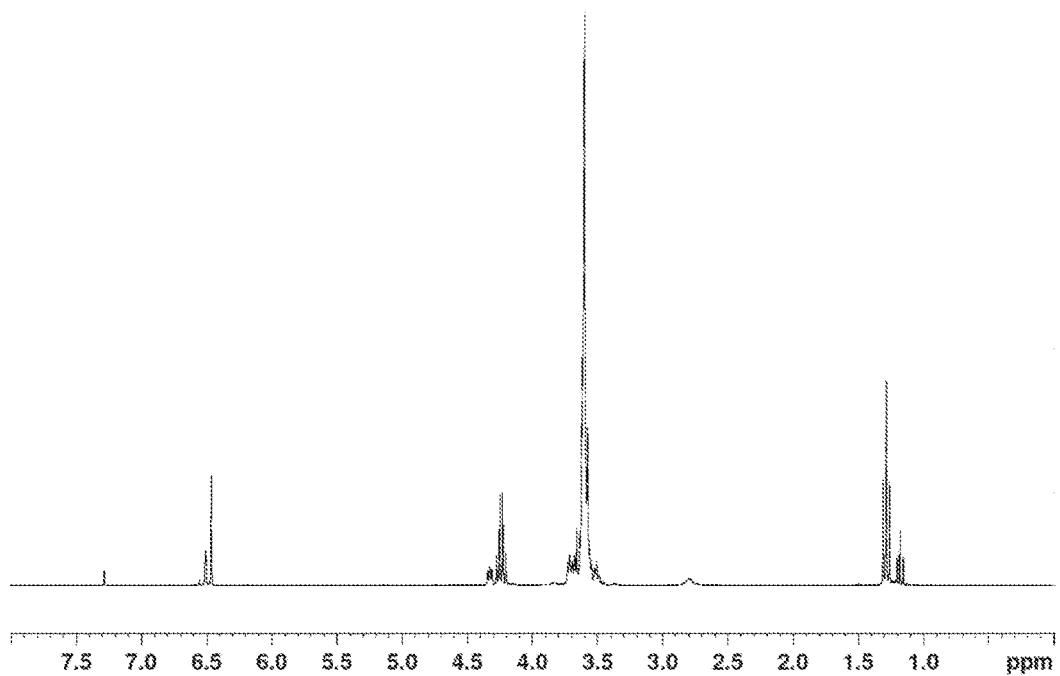
FIG. 2A: Full scale H-NMR of transesterification of DEMM with glycerol ethoxylate. Formation of new species can be confirmed in the 6.5 ppm methylene (double bond) region.
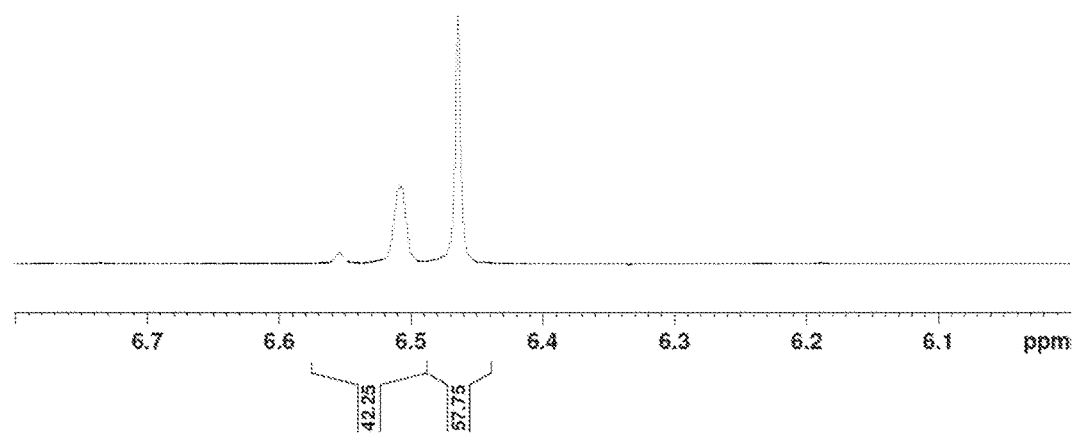
FIG. 2B. Integration of the two species seen in the 6.5 ppm region of the spectrum in 2A above confirms the amount of transesterified species is around 42% (with 58% residual DEMM).

WATER ABSORBING OR WATER SOLUBLE POLYMERS, INTERMEDIATE COMPOUNDS, AND METHODS THEREOF

CLAIM OF PRIORITY

This application claims the benefit of priority to U.S. Provisional Patent Applications 62/452,543 filed on Jan. 31, 2017 by Sullivan et al., 62/421,754 filed on Nov. 14, 2016 by Palsule et al., and 62/345,334 filed on Jun. 3, 2016 by Palsule et al., and to U.S. patent application Ser. No. 15/592,829 filed on May 11, 2017 by Palsule et al., Ser. No. 15/234,191 filed on Aug. 11, 2016 by Palsule et al., Ser. No. 15/437,164 filed on Feb. 20, 2017, and Ser. No. 15/472,379 filed on Mar. 29, 2017, the contents of which are each incorporated herein by reference in its entirety.

FIELD

Disclosed are novel polymers and polymeric compositions comprising a first component including a polymer formed from polymerizing one or more monomers including a 1,1-diester-alkene attached to a second component that is a hydrophilic component. The hydrophilic component preferably includes a hydrophilic polymer or a hydrophilic functional group. Preferred polymers are water absorbing polymers or polymers that dissolve in water. Also disclose are intermediate compounds, and related methods. The grafted polymer may be used in a variety of applications including as a surfactant, an ionomer, an antifouling agent, for petroleum recovery, for water treatment, as a flocculant, for hydrometallurgy, as a detergent, in a pharmaceutical process, or any combination thereof.

BACKGROUND

There is a need for new water absorbing polymer and new water soluble polymers for a variety of applications.

There is also a need for new hydrophilic polymers that are cross-linked so that they do not dissolve in water.

There is also a need for polymers capable of absorbing high levels of water.

SUMMARY

One aspect of the teaching herein is directed at a grafted polymer comprising: a first component including a polymer formed by polymerizing one or more monomers including a 1,1-disubstituted-1-alkene compound, attached to a second component that is a hydrophilic component, wherein the hydrophilic component includes a cation or a water-soluble polymer.

This aspect of the invention may be further characterized by one or any combination of the following features: the polymer of the first component has a first end and a second end and a backbone connecting the first and a second ends, the backbone including about 92 atomic percent or more carbon atoms; the hydrophilic component is a water-soluble polymer selected from the group consisting of a polyacrylamide, a polyvinyl alcohol, a polyacrylic acid, a polyalkoxide (e.g., a polyethylene glycol homopolymer or a polyethylene glycol copolymer), an water soluble amine containing polymer (e.g., polyamines, polyethyleneimines, and polymers including quaternary ammonium compounds), a copolymer of vinyl methyl ether and maleic anhydride, polyvinylpyrrolidone, a copolymer thereof, or any combination thereof; the second component includes a quaternary ammonium compound; the second component includes a polyalkoxide (preferably ethylene glycol homopolymer or copolymer); the polyalkoxide includes 65 weight percent or more ethylene oxide groups, based on the total weight of the polyalkoxide; the grafted polymer has a network structure (e.g., the grafted polymer is cross-linked, includes a multifunctional monomer, or the second component is attached to two or more 1,1-disubstituted-1-alkene compounds); the one or more monomers includes a multifunctional 1,1-disubstituted-1-alkene monomer (e.g., a multifunctional macromer) having two or more polymerizable alkene groups; about 20 atomic percent or more (preferably about 30 atomic percent or more, more preferably about 38 atomic percent or more, and most preferably about 46 atomic percent or more) of the monomers of the first component are directly attached to the second component; the first component is present in an amount of about 10 weight percent or more (preferably about 15 weight percent or more, more preferably about 20 weight percent or more, and even more preferably about 30 weight percent or more), based on the total weight of the graft polymer; the second component is present in an amount of about 20 weight percent or more (preferably about 30 weight percent or more, and more preferably about 40 weight percent or more), based on the total weight of the graft polymer; the total amount of the first component and the second component is about 50 weight percent or more (preferably about 70 weight percent or more, even more preferably about 90 weight percent or more, and most preferably about 97 weight percent or more), based on the total weight of the graft polymer; about 10 atomic percent or more of the monomers of the first component are 1,1-diester-1-alkenes that are free of direct attachment to the hydrophilic component; the grafted polymer consists essentially of the first component consisting only of one or more 1,1-diester-1-alkene compounds, and the second component consisting only of the water-soluble polymer or the cation; the grafted polymer is associated with an anion; the anion includes a sulfonate ion or a sulfate ion; the 1,1-disubstituted-1-alkene compound includes one or more 1,1-diester-1-alkenes; the grafted polymer includes a sufficient amount of the second component so that the grafted polymer is water soluble; or the grafted polymer includes about 30 to about 95 weight percent of the water-soluble polymer, based on the total weight of the grafted polymer.

Preferably the 1,1-disubstituted-1-alkene compound is a compound having a structure:

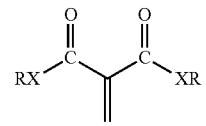

wherein R is a hydrocarbyl group which may contain one or more heteroatoms and X is oxygen or a direct bond (e.g, a methylene β-ketoester). More preferably, the 1,1-disubstituted-1-alkene compound is a methylene malonate having a structure:

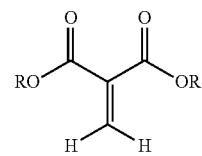

wherein R is separately in each occurrence alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene, or both of the R's form a 5-7 membered cyclic or heterocyclic ring (preferably R is separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the R groups form a 5-7 membered cyclic or heterocyclic ring).

Another aspect of the present teachings is directed at a polymeric composition including one or more of the grafted polymers according to the teachings herein. Preferably the polymeric composition includes about 10 weight percent or more of the grafted polymer, based on the total weight of the polymeric composition. Preferably, the polymeric composition includes; about 0.5 to about 90 weight percent of one or more compounds selected from the group consisting of a filler, a stabilizer, a process aid, a biocide, a polymer, a colorant, a salt, and any combination thereof.

Another aspect of the present teachings is a polymerizable composition including a 1,1-disubstituted-1-alkene compound grafted to a water-soluble polymer or to a compound including a cation (e.g., for polymerizing the grafted polymer according to the teachings herein). The water-soluble polymer may be grafted to one, two or more 1,1-disubstituted-1-alkene compounds. The grafted 1,1-disubstituted-1-alkene compound may be grafted to one or two water-soluble polymers (e.g., at opposing ends of the 1,1-disubstituted-1-alkene compound). The 1,1-disubstituted-1-alkene compound may be grafted to one or two cations (e.g., at opposing ends of the 1,1-disubstituted-1-alkene compound). The polymerizable composition preferably includes about 20 weight percent or more of grafted 1,1-disubstituted-1-alkene compounds. The polymerizable composition may optionally include one or more 1,1-disubstituted-1-alkene compounds that are free of graft (e.g., free of cation and free of water-soluble polymer). The polymerizable composition and/or the graft polymer may include one or more cross-linkers. For example, the polymerizable composition may optionally include a multi-functional 1,1-disubstituted-1-alkene compound having two or more polymerizable alkene groups. The polymerizable composition may include a catalyst for accelerating a polymerization reaction of the 1,1-disubstituted-1-alkene compound (e.g., the grafted 1,1-diester-alkene compound).

Another aspect according to the teachings herein is a method of forming a grafted compound comprising a step of grafting a 1,1-diester-1-alkene compound with a quaternary ammonium compound or with a water-soluble polymer.

These aspects may be characterized by one or any combination of the following features;
the 1,1-diester-1-alkene is grafted on each of the esters; the grafting step is catalyzed by an acid catalyst (preferably a bronsted acid) or an enzymatic catalyst; the grafting step includes a transesterification reaction; or the method includes a step of polymerizing the 1,1-diester-1-alkene compounds (preferably after the step of grafting).

Preferably, the water-soluble polymer is selected from the group consisting of a polyacrylamide, a polyvinyl alcohol, a polyacrylic acid, a polyalkoxide (e.g., a polyethylene glycol homopolymer or a polyethylene glycol copolymer), an water soluble amine containing polymer (e.g., polyamines, polyethyleneimines, and polymers including quaternary ammonium compounds), a copolymer of vinyl methyl ether and maleic anhydride, polyvinylpyrrolidone, a copolymer thereof, or any combination thereof.

Another aspect of the teachings herein is a method of forming a grafted polymer including a step of polymerizing a polymerizable composition, such as a polymerizable composition taught herein. The polymerization reaction may be catalyzed by a surface or by a catalyst. A particularly preferred catalyst is tetramethylguanidine.

Another aspect of the teachings herein is a conductive polymeric composition comprising: a grafted polymer (e.g., a grafted polymer as described herein) doped with one or more salts (e.g., at a concentration of about 20 weight percent or more, based on the total weight of the composition).

Another aspect of the teachings herein is a coating comprising a grafted polymer as described herein.

For various applications, the grafted polymer preferably is cross-linked or has a network structure.

In various aspects, the grafted polymer maybe water soluble and/or the grafted polymer may include a phase or component that is generally water soluble. For example, the polymer may include a water soluble polyalkoxide. To prevent the polymer from dissolving when exposed to water, the grafted polymer may have a sufficient amount of cross-linking (e.g, by employing a sufficient amount of a cross-linker) so that a network structure is formed. The amount of cross-linking preferably is sufficient so that the absorption of water by the polymer is constrained by the stretching of the polymer segments between crosslink sites.

BRIEF DESCRIPTION OF DRAWINGS

FIG. 1A is an illustrative full scale H-NMR of transesterification of DEMM with polyethylene glycol PEG 300. Formation of new species can be confirmed in the 6.5 ppm methylene (double bond) region.

FIG. 1B is an illustrative H-NMR spectrogram of DEMM grafted with polyethylene glycol PEG 300 polyol and including unreacted DEMM showing two species in the 6.5 ppm region of the spectrum in 1A. The amount of the transesterified species is around 35 percent and the amount of unreacted DEMM is about 65 percent.

FIG. 2A is an illustrative H-NMR spectrogram of transesterification of DEMM with glycerol ethoxylate. Formation of new species can be confirmed in the 6.5 ppm methylene (double bond) region.

FIG. 2B is an illustrative H-NMR spectrogram showing the integration of the two species seen in the 6.5 ppm region of the spectrum in FIG. 2A. The amount of transesterified species is around 42% and the amount of unreacted DEMM is about 58 percent.

DETAILED DESCRIPTION

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

Acid catalyst, as used herein, is an acidic species that catalyzes the transesterification reaction while minimizing or not contributing to side reactions. One or more as used herein means that at least one, or more than one, of the recited components may be used as disclosed. Nominal as used with respect to functionality refers to the theoretical functionality; generally, this can be calculated from the stoichiometry of the ingredients used. Heteroatom refer to atoms that are not carbon or hydrogen such as nitrogen, oxygen, sulfur, and phosphorus; heteroatoms may include nitrogen and oxygen. Hydrocarbyl, as used herein, refers to a group containing one or more carbon atom backbones and hydrogen atoms, which may optionally contain one or more heteroatoms. Where the hydrocarbyl group contains heteroatoms, the heteroatoms may form one or more functional groups well-known to one skilled in the art. Hydrocarbyl groups may contain cycloaliphatic, aliphatic, aromatic, or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl, and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. As used herein percent by weight or parts by weight refer to, or are based on, the weight or the compounds or compositions described unless otherwise specified. Unless otherwise stated parts by weight are based 100 parts of the relevant composition.

First Component

The first component may be a homopolymer consisting substantially of or even entirely of a 1,1-disubstiuted-1-alkene compound, or a copolymer including one or more 1,1-disubsituted-1-alkene compounds. The copolymer may include two or more different 1,1-disubstituted-1-alkene compounds. The copolymer may include a monomer that is not a 1,1-disubstituted-1-alkene compound, but is capable of copolymerizing with the 1,1-disubstituted-1-alkene compound. The copolymer may be a random copolymer or a block copolymer. Some or all of the 1,1-disubstituted-1-alkene compound is attached to the second component. The first component may include a cross-linker for cross-linking the copolymer of the first component and/or for forming a network structure.

1,1-Disubstituted-1-Alkene Compound

The composition disclosed include 1,1-disubstituted-1-alkene compounds which preferably are 1,1-dicarbonyl substituted alkene compounds. Preferred 1,1-dicarbonyl substituted alkene compounds are 1,1-dicarbonyl substituted ethylene compounds. 1,1-dicarbonyl substituted ethylene compounds refer to compounds having a carbon with a double bond attached thereto and which is further bonded to two carbonyl carbon atoms. Exemplary compounds are shown in Formula 1:

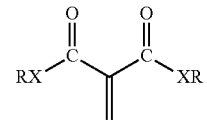

Formula 1 wherein R is a hydrocarbyl group which may contain one or more heteroatoms and X is oxygen or a direct bond (such as a methylene β-ketoester). Exemplary classes of 1,1-dicarbonyl substituted ethylenes are the methylene malonates, methylene beta-keto ester or diketones. Methylene malonates are exemplified by Formula 2:

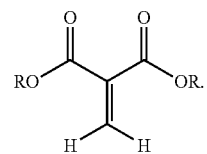

Formula 2

R may be separately in each occurrence alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene, or both of the R's form a 5-7 membered cyclic or heterocyclic ring. R may be separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the R groups form a 5-7 membered cyclic or heterocyclic ring. The recited groups may be substituted with one or more substituents, which do not interfere with the reactions disclosed herein. Preferred substituents include halo alkylthio, alkoxy, hydroxyl, nitro, azido, cyano, acyloxy, carboxy, or ester. R may be separately in each occurrence $C_1$-$C_{15}$ alkyl, $C_3$-$C_6$ cycloalkyl, $C_{4-18}$ heterocyclyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. R may be separately in each occurrence a $C_{1-4}$ alkyl. R may be separately in each occurrence methyl or ethyl. R may be the same for each ester group on the 1,1-dicarbonyl substituted ethylenes. Exemplary compounds are dimethyl, diethyl, ethylmethyl, dipropyl, dibutyl, diphenyl, and ethyl-ethyl gluconate malonates; or dimethyl and diethyl methylene malonate (R is either methyl or ethyl).

The 1,1-dicarbonyl substituted ethylene compounds disclosed herein exhibit a sufficiently high purity so that it can be polymerized. The purity of the 1,1-dicarbonyl substituted ethylenes may be sufficiently high so that 70 mole percent or more, preferably 80 mole percent or more, more preferably 90 mole percent or more, even more preferably 95 mole percent or more, and most preferably 99 mole percent or more of the 1,1-dicarbonyl substituted ethylenes is converted to polymer during a polymerization process. The purity of the 1,1-dicarbonyl substituted ethylenes is about 96 mole percent or greater, about 97 mole percent or greater, about 98 mole percent or greater, about 99 mole percent or greater, or about 99.5 mole percent or greater, based on the total weight of the 1,1-dicarbonyl substituted ethylenes. The 1,1-dicarbonyl substituted ethylenes contain 4 mole percent or less of 1,1-dicarbonyl substituted-1,1 bis (hydroxymethyl)-methanes, 3 mole percent of less of 1,1-dicarbonyl substituted-1,1 bis (hydroxymethyl)-methanes, 2 mole percent of less of 1,1-dicarbonyl substituted-1,1 bis (hydroxymethyl)-methanes, 1 mole percent of less of 1,1-dicarbonyl substituted-1,1 bis (hydroxymethyl)-methanes, or 0.5 mole percent of less of 1,1-dicarbonyl substituted-1,1 hydroxymethyl-methanes. The concentration of any impurities containing a dioxane group preferably is about 2 mole percent or less, more preferably about 1 mole percent or less, even more preferably about 0.2 mole percent or less, and most preferably about 0.05 mole percent or less, based on the total weight of the 1,1-dicarbonyl substituted ethylenes. The total concentration of any impurity having the alkene group replaced by an analogous hydroxyalkyl group (e.g., by a Michael addition of the alkene with water) preferably is about 3 mole percent or less, more preferably about 1 mole percent or less, even more preferably about 0.1 mole percent or less, and most preferably about 0.01 mole percent or less, based on the total moles in the 1,1-dicarbonyl substituted ethylenes. Preferred 1,1-dicarbonyl substituted ethylenes are prepared by a process including one or more (e.g., two or more) steps of distilling a reaction product or an intermediate reaction product (e.g., a reaction product or intermediate reaction product of a source of formaldehyde and a malonic acid ester).

The functional compound may include one or more methylene malonates which may be the same or different.

The 1,1-disubstituted-1-alkene compound may include one or any combinations of the 1,1-disubstituted alkene compounds and 1,1-disubstituted ethylene compounds disclosed in U.S. Pat. No. 9,249,265 B1, issued Feb. 2, 2016 (see e.g., column 5, line 44 through column 10, line 30), incorporated herein by reference in its entirety.

Particularly preferred monomers include methyl propyl methylene malonate, dihexyl methylene malonate, di-isopropyl methylene malonate, butyl methyl methylene malonate, ethoxyethyl ethyl methylene malonate, methoxyethyl methyl methylene malonate, hexyl methyl methylene malonate, dipentyl methylene malonate, ethyl pentyl methylene malonate, methyl pentyl methylene malonate, ethyl ethylmethoxy methylene malonate, ethoxyethyl methyl methylene malonate, butyl ethyl methylene malonate, dibutyl methylene malonate, diethyl methylene malonate (DEMM), diethoxy ethyl methylene malonate, dimethyl methylene malonate, di-N-propyl methylene malonate, ethyl hexyl methylene malonate, methyl fenchyl methylene malonate, ethyl fenchyl methylene malonate, 2-phenylpropyl ethyl methylene malonate, 3-phenylpropyl ethyl methylene malonate, and dimethoxy ethyl methylene malonate.

The 1,1-disubstituted-1-alkene compound may be a compound prepared by a transesterification, such as described in U.S. Provisional Patent Application No. 62/421,754, filed on Nov. 14, 2016, the contents of which are incorporated herein by reference in its entirety.

Cross-Linker

The first component may include a cross-linker. The cross-linker may be employed for cross-linking the polymer and/or for forming a network structure. The cross-linker may be a compound that copolymerizes with the other monomers of the first component. For example, the cross-linker may include one or more (preferably two or more) alkene groups. Preferably, each alkene group is capable of polymerizing on a separate polymer molecules to form a link between the polymer molecules. As another example, the cross-linker may attach to a functional group (i.e., a functional group other than the alkene group) on each of two polymer molecules to connect the two polymer molecules. The cross-linker may be a multifunctional monomer, such as described herein.

Multifunctional Monomer

The 1,1-disubstituted-1-alkene compound may include a multi-functional compound including two or more alkene groups. Examples of multi-functional compounds that may be employed herein include those described in U.S. Pat. No. 9,249,265 B1, issued Feb. 2, 2016 (see e.g., column 9, line 12 through column 9, line 46), incorporated herein by reference in its entirety. Other examples of multi-functional compounds having a plurality of alkenyl groups includes those described in US Patent Application Publication US 2016/0068616 A1 (see e.g., paragraph 0042), incorporated herein by reference. For example, some or all of the 1,1-disubstituted alkenes can also be multifunctional having more than one core unit and thus more than one alkene group. Exemplary multifunctional 1,1-disubstituted alkenes are illustrated by the formula:

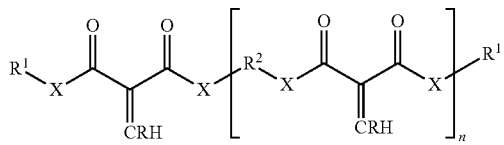

wherein $R^1$, $R^2$ and X are as previously defined; n is an integer of 1 or greater; and R is a hydrocarbyl group, and the 1,1-disubstituted alkene has n+1 alkenes. Preferably n is 1 to about 7, and more preferably 1 to about 3, and even more preferably 1. In exemplary embodiments $R^2$ is, separately in each occurrence, straight or branched chain alkyl, straight or branched chain alkenyl, straight or branched chain alkynyl, cycloalkyl, alkyl substituted cycloalkyl, aryl, aralkyl, or alkaryl, wherein the hydrocarbyl groups may contain one or more heteroatoms in the backbone of the hydrocarbyl group and may be substituted with a substituent that does not negatively impact the ultimate function of the compounds or polymers prepared from the compounds. Exemplary substituents are those disclosed as useful with respect to $R^1$. In certain embodiments $R^2$ is, separately in each occurrence, $C_{1-15}$ straight or branched chain alkyl, $C_{2-15}$ straight or branched chain alkenyl, $C_{5-18}$ cycloalkyl, $C_{6-24}$ alkyl substituted cycloalkyl, $C_{4-18}$ aryl, $C_{4-20}$ aralkyl or $C_{4-20}$ aralkyl groups. In certain embodiments $R^2$ is separately in each occurrence $C_{1-8}$ straight or branched chain alkyl, $C_{5-12}$ cycloalkyl, $C_{6-12}$ alkyl substituted cycloalkyl, $C_{4-18}$ aryl, $C_{4-20}$ aralkyl or $C_{4-20}$ alkaryl groups.

If employed, the amount of the multi-functional compound preferably is sufficiently low so that the glass transition temperature of the polymer is not greatly affected by the network structure formed by the cross-links formed upon polymerization. For example, any increase in the glass transition temperature due to the multi-functional compound preferably is about 50° C. or less. Preferably the amount of the multi-functional compound is about 50 weight percent or less, more preferably about 30 weight percent or less, and most preferably about 12 weight percent or less, based on the total weight of the 1,1-disubstituted-1-alkene compounds (e.g., in the polymerizable composition or in the grafted polymer). The amount of the multi-functional compound preferably is sufficiently high so that a network or other cross-linked structure is obtained and/or for accelerating the polymerization reaction. A network structure may be particularly useful in avoiding the grafted polymer from being entirely absorbed in water. Acceleration in the polymerization reaction may be particularly useful for reducing setting time of an adhesive or coating including the grafted polymer. The amount of the multi-function compound preferably is present in an amount of about 0.2 weight percent or more, more preferably about 0.5 weight percent or more, even more preferably about 1.5 weight percent or more, and most preferably about 3.6 weight percent or more, based on the total weight of the 1,1-disubstituted-1-alkene compounds.

Second Component

Some or all of the 1,1-disubstituted-1-alkene compound (e.g., the 1,1-diester-1-alkene compound) is grafted with a second component that imparts hydrophilic characteristics to the grafted compound. The second component (i.e., the hydrophilic component) may be a water-soluble polymer or a functional compound having ionic characteristics.

Hydrophilic component may include an oligomeric polymer (e.g., having a molecular weight from about 200 g/mole to about 8500 g/mole) or a high molecular weight polymer (having a molecular weight greater than 8500 g/mole). Such polymer include polyacrylamide homopolymers and copolymers, polyvinyl alcohol hom polymers and copolymers, polyacrylic acid homopolymers and copolymers, polyalkoxide homopolymers and copolymers (e.g., polyethylene oxide), amine containing polymers (e.g., polyamines, polyethyleneimines, and polymers including quaternary ammonium compounds), copolymers of vinyl methyl ether and maleic anhydride, and polyvinylpyrrolidone homopolymers and copolymers.

The second component may include or consist essentially of one or more quaternary ammonium compounds, such as a salt having a cation with the following structure:

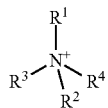

where the nitrogen is bonded to four carbon atoms. Preferably, the nitrogen atom is directly attached to one or more alkoxy groups. For example, the quaternary ammonium compound may have the structure:

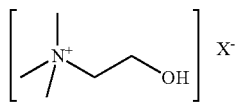

where $X^-$ is a counter anion. Preferably, $R^1$, $R^2$, $R^3$, and $R^4$ are each alkyl or alkoxy groups, and most preferably $C_1$, $C_2$, $C_3$, or $C_4$ alkyl or $C_1$, $C_2$, $C_3$, or $C_4$ alkoxy groups. The number of alkoxy groups on the quaternary ammonium compound may be one, two or more, and is most preferably one.

The counter anion for the quaternary ammonium compound may be any anion. Examples of anions include halogen anions (fluoride ion, chloride ion, bromide ion, or iodide ion), hydroxide ion, acetate ion, chlorate ion, sulfate ion, nitrate ion, perchlorate ion, and sulfite ion, nitrite ion, sulfate anions, sulfite anions, and carbonate ions. Particularly preferred anions include sulfite ions, nitrate ions, and carbonate ions.

Grafting or Transesterification Reaction

The second component may be grafted onto the 1,1-disubstituted-1-alkene compound (e.g., the 1,1-diester-1-alkene compound) using any method capable of connecting the compounds. Preferably the 1,1-disubstituted-1-alkene compound is directly connected to the second component by a covalent bond. A preferred reaction for grafting the second component is a transesterification reaction. The transesterification reaction may employ one or more catalysts. It will be appreciated that the grafting reaction may occur before or after the polymerization of the 1,1-disubstituted-1-alkene compound. Preferably the grafting reaction is performed prior to the polymerization reaction.

An illustrative grafting reaction is shown below, where a 1,1-disubstituted-1-alkene compound (e.g., DEMM) is reacted with a quaternary ammonium salt by a transesterification reaction using a catalyst (e.g., an acid catalyst or an enzymatic catalyst).

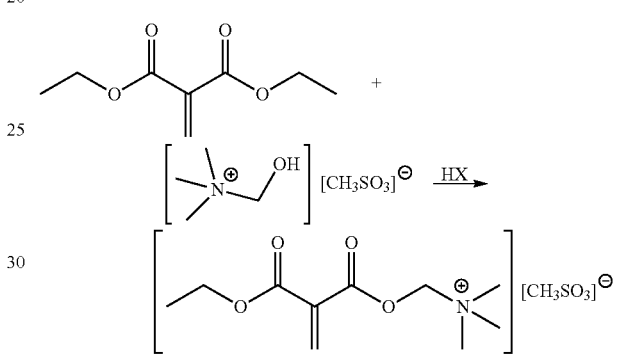

Another illustrative grafting reaction is shown below, where a 1,1-disubstituted-1-alkene compound (e.g., DEMM) is reacted with a water-soluble polymer (e.g., polyethylene glycvol) by a transesterification reaction.

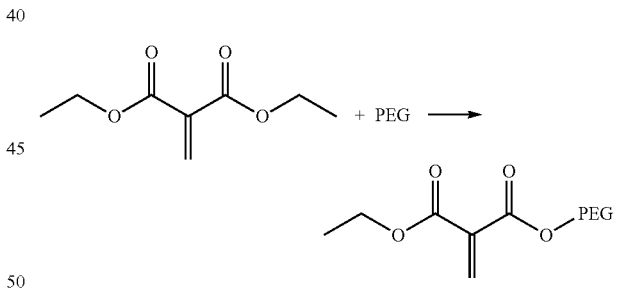

Catalyst

The transesterification reactions according to the teachings herein are typically performed in the presence of one or more catalysts. The transesterification catalyst may be an acid, an ester of such acid or an enzyme. The transesterification catalyst may be an enzyme. The transesterification catalyst may be a lipase enzyme. A transesterification process utilizing an enzyme is disclosed in US 2014/0329980, incorporated herein by reference for all purposes in its entirety.

The transesterification catalyst may be one or more acids having a pKa in a polar aprotic solvent of about −5 to about 14 or esters of the acids. The acid or the ester of the acid may be present in an amount of about 3.0 molar equivalents or less of the acid or the ester of acid per molar equivalent of the ester containing compounds transesterified. When the catalyst is an acid or an ester of an acid the method may be performed at a temperature of about 20° C. to about 160° C. The transesterification catalyst may be a lipase enzyme catalyst. When the catalyst is a lipase enzyme catalyst the transesterification step is performed at an elevated temperature between about 20° C. and 70° C. During the transesterification reaction, volatile by-products may be formed and removed from the reaction mixture. The volatile by-products may be removed from the reaction mixture by applying a vacuum. The volatile by-products may be alcohols.

The catalyst may be an acid or an ester thereof. The transesterification process using an acid or ester is disclosed in U.S. patent application Ser. No. 14/814,961 filed Jul. 31, 2015, incorporated herein by reference for all purposes in its entirety. Any acid or ester thereof that catalyzes transesterification while minimizing side reactions may be used. In some embodiments the acid or acid utilized to form an ester is an acid having a pKa in a polar aprotic solvent, such as acetonitrile or dioxane, as disclosed hereinafter. In particular the pKa is chosen to efficiently catalyze the transesterification reaction while minimizing side reaction and the concentration of catalyst in a reaction mixture. The acid used may have a pKa of about −5 or greater, about −3 or greater, or about 1.0 or greater. The acid used may have a pKa of about 14 or less, about 11 or less, or about 9 or less. The acid can be a Bronsted acid having a pKa as disclosed. The catalyst may be a superacid or an ester thereof. Superacid means an acid having an acidic strength greater than the strength of 100 percent sulfuric acid. Ester thereof, in the context of the acid catalysts, refer to compounds wherein the hydrogen on the acid is replaced with a hydrocarbyl group, preferably an alkyl group. Superacids are acids having a strength greater than the strength of 100 percent sulfuric acid, a pKa less than 100 percent sulfuric acid, that is less than 8, more preferably less than about 5, and most preferably less than about 2. The measurement of acid strength is based on Kutt et al. "Equilibrium Acidities of Super Acids," Journal of Organic Chemistry Vol 76 pages 391 to 395, 2011, published on the Web Dec. 17, 2010, which is incorporated herein by reference. Exemplary super acids include trifluoromethanesulfonic acid (triflic acid), sulfated tin oxide, triflated tin oxide, sulfated zirconia, triflated zirconia, and triflated HZSM-5. The most preferred super acids are triflic acid and fluorosulfonic acid.

Exemplary acid catalysts include triflic acid, fluorosulfonic acid, and sulfuric acid. For reactions requiring monosubstitution (only one hydroxyl group on the alcohol is being replaced by transesterification), weaker acids with pKa values equal to or higher than sulfuric acid may be desired. Examples of such acids include sulfuric acid or methanesulfonic acid. For reactions requiring disubstitution (two hydroxyl groups on the alcohol are being replaced by transesterification), stronger acids with pKa values equal to or lower than sulfuric acid may be desired. Examples of such acids include sulfuric acid, fluorosulfonic acid, and triflic acid. For reactions requiring polysubstitution (more than 2 hydroxyl groups on the alcohol), choice of acid catalysts can be similar to that for disubstitution reactions but reaction time may need to be increased. Esters of acids useful as catalysts include alkyl triflates.

The catalyst can be mixed with the reactants or can be supported on a substrate such as a membrane or an inert carrier such as a porous support structure (the catalysts can be heterogeneous). Catalysts which are not supported are commonly referred to as homogeneous. The catalyst can be used in any concentration that catalyzes the transesterification reaction. The amount of catalyst utilized for the reaction depends on the type of catalyst being chosen. The concentration of catalyst is about 3 molar equivalents or less per equivalent of the ester compounds undergoing transesterification; about 1 molar equivalents or less; about 0.5 molar equivalents or less; about 0.1 molar equivalents or less. The concentration of catalyst is about 0.01 molar equivalents or greater per equivalent of the ester compounds undergoing transesterification; and most preferably about 0.1 molar equivalents or greater. Higher concentrations of catalysts than recited may be utilized. As disclosed in Malofsky et al., U.S. Pat. Nos. 8,609,885 and 8,884,051; and Malofsky et al. WO 2013/059473 the presence of acid in the 1,1-disubstituted alkene compounds recovered can present problems with respect to use of the compounds and low concentrations of acid in the products in use is desired. If high levels of acid are contained in the final product, additional purification or removal steps may be required. The amounts recited achieve the balance between efficient catalysis and the need for low acid concentrations in the product for use. In embodiments when the catalyst is selected from sulfuric acid or those acids having pKa values less than that of sulfuric acid, the concentration of such catalysts in the reaction mixture is preferably at the upper end of the ranges recited herein.

The catalyst may include or consist entirely of an enzymatic catalyst. Any enzymatic catalyst suitable for catalyzing the transesterification reaction may be used. Various enzymatic catalysts are described in U.S. Pat. No. 7,972,822 B2 (by Gross et al., issued on Jul. 5, 2011, see for example column 8, lines 2-4 and 7-35), U.S. Pat. No. 5,416,927 A (by Zaks et al., issued May 31, 1994, see for example column 2, line 64 to column 3, line 12), U.S. Pat. No. 5,288,619 A (by Brown et al., issued Feb. 22, 1994, see for example column 4, line 18 to column 5, line 17), US Patent Application Publication 2016/177,349 A1 (by Addy et al., published Jun. 23, 2016, see for example paragraphs 0046-0048), U.S. Patent Application Publication 2014/0017741 A1 (by Nielsen et al., published Jan. 16, 2014, see for example paragraphs 0026-0029); the contents of which are each incorporated herein by reference.

Many different enzymes may be employed in enzymatic catalytic transesterification reactions for wax esters, including those that are derived/obtained from biological organisms, those made synthetically, and those that are entirely artificial, whether made biologically and/or synthetically. For those enzymes that are lipases, these may include, one, some, any, or any combination of lipases derived from the following organisms: *Aspergillus niger, Aspergillus oryzae, Bacillus subtilis, Bacillus thermocatenulatus, Burkholderia cepacia, Burkholderia glumae, Candida rugosa, Candida antarctica A, Candida antarctica B, Candida cylindracea, Candida parapsilosis, Chromobacterium viscosum, Geotrichum candidum, Geotrichum sp., Mucor miehei, Humicola lanuginose, Penicillium camembertii, Penicillium chrysogenum, Penicilium roquefortii, Pseudomonas cepacia, Pseudomonas aeruginosa, Pseudomonas fluorenscens, Pseudomonas fragi, Pseudomonas alcaligenes, Pseudomonas mendocina, Rhizopus arrhizus, Rhizomucor miehe, Staphylococcus hyicus, Staphylococcus aereus, Staphylococcus epidermidis, Staphylococcus warneria, Staphylococcus xylosus, Thermomyces lanuginosus, Aspergillus* sp., *Bacillus* sp., *Burkholderia* sp., *Candida* sp., *Chromobacterium* sp., *Geotrichum* sp, *Mucor* sp, *Humicola* sp, *Penicillium* sp, *Pseudomonas* sp, *Rhizopus* sp., *Staphylococcus* sp, and *Thermomyces* sp. The lipase may include or consist essentially of one or any combination of the following: a lipase from *Thermomyces lanuginosus* marketed under the tradenames LIPOZYME TL IM or LIPEX by Novozymes A/S of Bagsvaerd, Denmark and immobilized on a substrate also manufactured by Novozymes; the lipase may be that marketed under the tradename NOVOZYM by Novozymes, A/S derived from *Candida antarctica*; those marketed under the tradenames CALB L, NOVOZYME 435, NOVOCOR AD L, AND LIPOLASE 100L by Novozymes; those marketed under the tradenames CALB, CALA, and CRL by c-LEcta, GMBH of Leipzig, Germany; those marketed under the tradenames LIPASE A "AMANO" 12, LIPASE AY "AMANO" 30SD, LIPASE G "AMANO" 50, LIPASE R "AMANO", LIPASE DF "AMANO" 15, LIPASE MER "AMANO", and NEWLASE F by Amano Enzyme Inc. of Nagoya, Japan; those marketed under the tradenames LIPASE MY, LIPASE OF, LIPASE PL, LIPASE PLC/PLG, LIPASE QLM, LIPASE QLC/QLG, LIPASE SL, and LIPASE TL by Meito Sangyo Co., Ltd., of Nagoya, Japan, a lipase from *Candida antarctica* A, a lipase from *Candida antarctica* B, and a lipase from *Candida rugosa*. In various implementations, the lipases preferably have at least 60%, at least 70%, at least 80%, at least 90%, at least 95%, at least 96%, at least 97%, at least 98%, or even at least 99% identity to any of the lipases disclosed herein, and in the patent applications disclosed herein, all of which have been previously incorporated by reference.

Polymerization of the Grafted 1,1-Disubstituted-1-Alkene

The grafted 1,1-disubstituted-1-alkene compound may be polymerized by reacting the alkene group onto a growing polymer chain. Preferably about 70% or more, even more preferably about 90% or more, and most preferably about 98% or more of the alkene groups are polymerized. Preferably, the polymer includes a sufficient amount of the hydrophilic component (e.g. the water-soluble polymer and/or the cation containing compound) so that the resulting grafted polymer is hydrophilic or water-soluble. The polymerization reaction may be catalyzed (e.g., using tetramethylguanidine).

The polymerization of a grafted 1,1-disubstituted alkene including a water-soluble polymer is illustrated below.

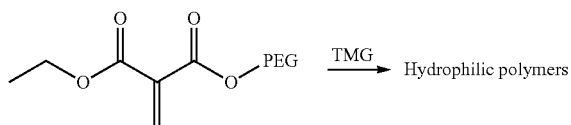

The polymerization of a grafted 1,1-disubstituted alkene including a cation containing compound is illustrated below.

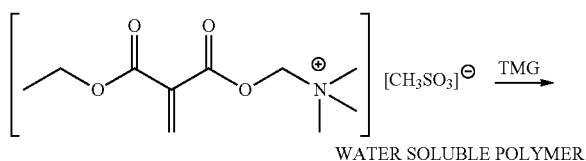

The polymerization reaction may occur at one or more reaction temperatures sufficiently high for converting the monomer into polymer. As the polymerization reaction progresses, the polymerizable composition may become a viscous liquid, a glassy liquid (e.g., below the glass transition temperature of the polymer) or even a solid (e.g., below the melting temperature of the polymer). Preferably, the reaction temperature is above the glass transition temperature of the resulting polymer (e.g., of the first component). Preferably, the reaction temperature is above any melting temperature of the resulting polymer. As an alternative, the process may include an initial polymerization at a relatively low temperature (e.g., below any melting temperature and/or below the glass transition temperature of the polymer) and then the process may include a secondary polymerization reaction at a higher temperature (e.g., above the melting temperature and/or above the glass transition temperature of the polymer). The reaction temperature and reaction time may be selected to provide a desired level of polymerization and/or a desired level of cross-linking.

Polymerizable System (i.e., Polymerizable Composition)

One aspect according to the teachings herein, is directed at a polymerizable system including the grafted 1,1-disubstituted alkene compound (e.g., grafted with the quaternary ammonium compound or with a water-soluble polymer) and preferably further including one or more 1,1-disubstituted alkene compounds (e.g., a methylene malonate monomer) that is free of any such graft. The methylene malonate monomer may be selected so that it will copolymerize with the alkenyl groups of the grafted compound. It will be appreciated that the grafted compound may include a 1,1-disubstituted-1-alkene compound that is the same or different from the methylene malonate monomer.

Any of the methylene malonate compounds described herein with respect to the graft compound having an alkenyl group for the may be employed as an additional monomer in the polymerizable composition. It will be appreciated that methylene malonate monomer may be replaced in part or in whole with dimers, trimers, or longer oligomers (e.g., having a degree of polymerization of about 4 to 50, about 4 to 15, or about 4 to 8).

The polymerizable system may include a sufficient amount of a stabilizer to prevent or minimize polymerization of the polymerizable system. The process may include a step of activating the polymerizable system for polymerizing the methylene malonate monomers and alkenyl group(s) attached to the grafted compound.

It will be appreciated that the polymerizable system may be used to form a grafted polymer that is a block copolymer including a first block including one or more 1,1-disubstituted alkene compounds and a second block including the water-soluble polymer. The amount of the first polymer block preferably is about 10 weight percent or more, more preferably about 20 weight percent or more, even more preferably about 25 weight percent or more, and most preferably about 30 weight percent or more, based on the total weight of the block copolymer. The amount of the first block may be about 90 weight percent or less, about 80 weight percent or less, about 70 weight percent or less, about 60 weight percent or less, or about 50 weight percent or less, based on the total weight of the block copolymer.

The amount of the water-soluble polymer in the block copolymer preferably is about 10 weight percent or more, more preferably about 20 weight percent or more, even more preferably about 30 weight percent or more, even more preferably about 40 weight percent or more, and and most preferably about 50 weight percent or more, based on the total weight of the block copolymer. The amount of the water-soluble polymer may be about 90 weight percent or less, about 80 weight percent or less, about 75 weight percent or less, or about 70 weight percent or less, based on the total weight of the block copolymer. The ratio of the weight of the first component to the weight of the water-soluble polymer in the block copolymer may be about 0.05 or more, about 0.10 or more about 0.20 or more or about 0.45 or more, or about 0.60 or more. The ratio of the weight of the first component to the weight of the water-soluble polymer may be about 10 or less, about 8 or less, about 6 or less, about 4 or less, about 3 or less, or about 2 or less.

The grafted 1,1-disubstituted alkene compounds and/or polymerizable system may be used for a film or coating. The film or coatings may have a thickness of about 0.001 μm or more, about 0.1 μm or more, about 1 μm or more, or about 2 μm or more. The coating or film preferably has a thickness of about 200 μm or less, more preferably about 50 μm or less, and most preferably about 20 μm or less.

The grafted polymer may be used in a polymeric composition including about 10 weight percent or more of the grafted polymer and about 0.5 to about 90 weight percent of one or more compounds selected from the group consisting of a filler, a stabilizer, a process aid, a biocide, a polymer, a colorant, a salt, and any combination thereof. For example, the polymeric composition may include a sufficient amount of a salt so the polymeric composition is an electrical conductor.

The second component may impart useful characteristics to the 1,1-disubstituted alkene compound (or the resulting grafted polymer) for use in oil field applications. For example, the grafted compound may be used as an oil-wetting agent, a bactericide, or a corrosion inhibitor.

The compositions, compounds and grafted polymers according to the teachings herein may be employed in various applications that take advantage of feature of one or both of the components of the grafted polymer. In particular, these materials may be employed in electronics (conducting polymers), as a surfactant, an ionomer, in a pharmaceutical process, in petroleum recovery in water treatment, as a flocculant, in a hydrometallurgy process, or as a detergent. Other applications include as a hydrophilic coating. For example, such a coating may be useful for anti-fouling applications. Without being bound by theory, it is believed that the high amount of hydration may provide a surface difficult for proteins and microorganisms to attach to. As such, the materials according to the teachings herein may prevent or reduce the accumulation of bio-organisms on a surface. These may be used for protecting against fouling by plants, algae, microorganisms, or animals. The material and compositions according to the teachings herein may be particularly used on surfaces that are at least partially submerged in a body of water containing organisms capable of fouling or otherwise attaching to the surface. They may be used for preventing fouling by calcerous fouling organisms include mussels (e.g., zebra mussels), mollusks, barnacles, and other organisms that form a hard calcium carbonate containing structure. They may be used for preventing fouling by non-calcerous organisms include algae, biofilm, seaweed and other organisms that lack a calcium carbonate containing structure. The materials and compositions according to the teachings herein may be used for removing water from surfaces and/or for keeping surfaces dry. The materials and compositions according to the teachings herein may be used for converting liquid waste to a stable solid or other structure where the liquid is absorbed by the grafted polymer. This may be particularly useful where the liquid includes chemically hazardous compounds, biologically hazardous materials, toxic materials, or environmentally hazardous substances.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

EXAMPLES

Example 1

Example 1 is a reaction mixture including a methylene malonate monomer grafted with a polyalkylene glycol and unreacted methylene malonate monomer. The grafting reaction is carried out using PEGylation process.

CARBOWAX™ PEG 300 polyethylene glycol (commercially available from DOW CHEMICAL COMPANY) is purified by passing through an alumina column to residual base catalyst. The polyethylene glycol has a number average molecular weight of about 285 to 300 g/mole, a hydroxyl number of about 340 to 394 mg KOH/g, a melting range of about −15° C. to about −8° C., and a heat of fusion of about 37 cal/g. A 250 mL round bottom flask is charged with about 30 g (0.17 mol) of DEMM, about 3 g (10 wt % of the DEMM) of CLEA 102B4enzyme and about 16.6 g (0.083 mol) of the PEG 300 (alumina passed). The flask is connected to a rotary evaporator with a vacuum of about 200 mm Hg and heated to about 45° C. for 2 hrs. The vacuum removes ethanol as a reaction by-product. The enzyme is then filtered from the reaction mixture using a cotton plug in 20 ml syringe. NMR results indicate that about 35 percent of the DEMM is reacted to the PEG and about 65 percent of the DEMM remains as unreacted monomer in the reaction mixture. FIG. 1 shows the NMR for the reaction mixture.

The grafted DEMM may have a structure including a central polymer portion including a polyalkoxide and terminal methylene malonate groups having one or more (or all) of the features illustrated below:

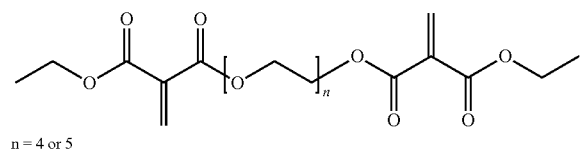

n = 4 or 5

The reaction mixture of the grafted DEMM is drawn down on a pre-initiated (0.1% Na-benzoate in butyl cellosolve) cold rolled steel panel using a Meyer Rod 10 resulting in a 25-micron thick coating after full cure at room temperature for 24 hours followed by heating at 82° C. for 1 hour. The coating displays hydrophilic character with water wetting the surface with ease and eventually permeating through the coating layer on continued exposure. A similar coating drawn down with only DEMM monomer demonstrates no hydrophilic character. This demonstrates the hydrophilicity imparted by polyethylene glycol in DEMM based coatings.

Example 2

Example 2 is a reaction mixture including a polyalkylene glycol grafted onto a methylene malonate monomer and unreacted methylene malonate monomer. The grafting of the polyalkylene glycol is carried out using an acid catalyzed transesterification process.

A three neck (250 mL) round bottom flask with a distillation head, thermometer, vacuum adapter, and a collection flask are assembled using high vacuum grade grease along with a heating mantle (and thermocouple) and a magnetic stir bar. To this round bottom flask set-up, a mixture of about 20 g (about 0.12 mol) of DEMM, about 4.6 g (about 0.023 mol) of CARBOWAX™ PEG 200 polyethylene glycol (commercially available from DOW CHEMICAL COMPANY), about 0.02 g (about 1000 ppm) of MeHQ and about 0.3 ml (about 0.0058 mol) of $H_2SO_4$ is charged. CARBOWAX™ PEG 200 polyethylene glycol has a weight average molecular weight of about 190 to 210 g/mole, an average hydroxyl number of about 535 to about 590 mg KOH/g, and a melting point below about −65° C. A reduced pressure of about 400 mm Hg is maintained during the reaction using a vacuum pump. The reaction mixture is then heated to about 130° C. and stirred for about 2 hours. Ethanol is collected as a reaction byproduct. The amount of grafting of the PEG onto the DEMM is calculated using NMR. About 45 percent of the DEMM is reacted with the PEG and about 55 percent of the DEMM remains as monomer.

The grafted compound may have a structure including a central polymer portion including a polyalkoxide and terminal methylene malonate groups having one or more (or all) of the features illustrated below:

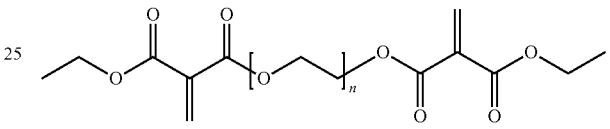

Example 3

Example 3 is a reaction mixture including a glycerol ethoxylate grafted onto a methylene malonate monomer and unreacted methylene malonate monomer. The grafting of the glycerol ethoxylate may be carried out using a transesterification process.

A 250 mL round bottom flask is charged with about 30 g (about 0.17 mol) of DEMM, about 3 g (about 10 parts per 100 parts of DEMM) of enzyme NOVOZYME 435 candida antartica isoform B (commercially available from NOVOZYME) and about 56 g (about 0.056 mol) of glycerol ethoxylate (having a number average molecular weight of about 1000, obtained from Sigma Aldrich). The flask is connected to a rotary evaporator with reduced pressure of about 200 mm Hg and is heated to about 55° C. for about 8 hours. Ethanol is removed as a reaction byproduct. The enzyme is then filtered from the product using cotton plug in a 20 ml syringe, for isolating the reaction mixture. NMR results are obtained of the reaction mixture and used to calculate the conversion of the glycerol ethoxylate to the end-capped product. About 40% of desired transesterified products (i.e., end-capped product) is observed. The NMR spectrum for the reaction mixture is shown in FIG. 2. It is believed that the reaction mixture includes disubstituted and trisubstituted glycerol ethoxylate reaction products. The resulting reaction mixture includes the grafted compound having one or more of the features as shown in the structures below.

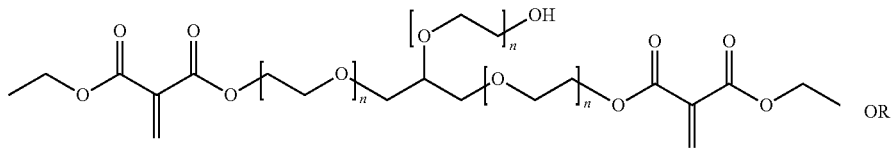

OR

-continued

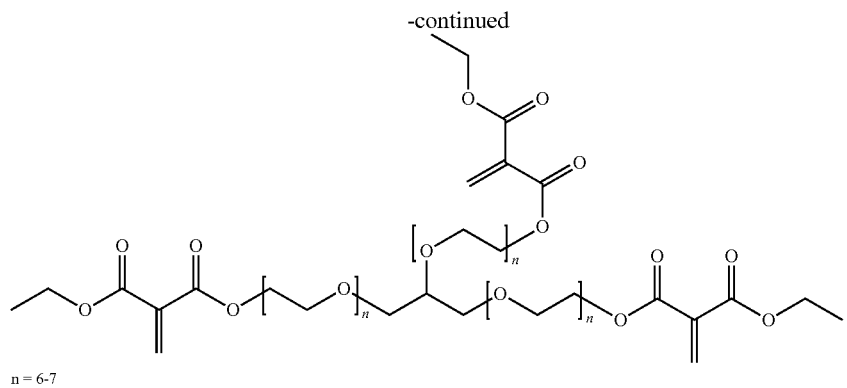

n = 6-7

The reaction mixture is drawn down on a pre-initiated (0.1% Na-benzoate in butyl cellosolve) cold rolled steel panel using a Meyer Rod 10 resulting in a about 25-micron thick coating after full cure at room temperature for about 24 hours followed by heating at about 82° C. for about 1 hour. The coating displays hydrophilic character with water wetting the surface with ease and eventually permeating through the coating layer on continued exposure. In comparison, a specimen prepared with the reaction mixture replaced with only DEMM and cured under the same conditions (e.g., resulting in a DEMM homopolymer) demonstrates no hydrophilic character. Thus, the DEMM grafted with glycerol ethoxylate may be used to impart hydrophilicity in a coating (e.g., in a methylene malonate coating, such as a DEMM based coatings).

Characterization of the Graft Polymer

The graft polymer may be evaluated for water solubility/hydrophilicity characteristics.

A primer solution of either about 0.1 wt % sodium benzoate or about 0.5 wt % tetramethylguanidine (i.e, TMG) in ethanol is drawn down onto a steel panel using a meyer rod. The solvent is allowed to flash off at room temperature. Then, 2 ml of a polymerizable composition (e.g., including the second component directly attached to a methylene malonate compound) is applied to the top of the panel and drawn down in a similar manner using a meyer rod. The coating is left to cure at room temperature overnight for about 18 hours.

The cured coating is tested by applying a single drop of reverse osmosis (i.e., RO) water to the surface and measuring the amount of time for the coating to be dissolved or the drop to be absorbed. The coating displays hydrophilic character with water wetting the surface of the coating with ease and eventually permeating through the coating layer and preferably removing the coating on continued exposure.

Several graft polymers are prepared by mixing a dimethyl methylene malonate monomer, diethyl methylene malonate functionalized with glycerol ethoxylate, and a cross-linker as shown in the table below and coatings were tested in the following manner. The polymerization is on the steel substrate treated with the primer solution as described above.

| | Composition | | | | |
|---|---|---|---|---|---|
| | FM1 | FM2 | FM3 | FM4 | FM5 |
| DEMM functionalized glycerol ethoxylate, weight % | 80 | 70 | 60 | 50 | 30 |
| Cross-linker, weight percent | 10 | 20 | 10 | 20 | 35 |
| D3M, weight percent | 10 | 10 | 30 | 30 | 35 |

After polymerizing the first component, the first component includes a random copolymer of the D3M, DEMM, and the cross-linker, where the cross-linker is a multi-functional 1,1-disubstituted-1-alkene compound having a plurality of polymerizable alkene groups. The second component (i.e, the hydrophilic component) consists essentially of the glycerol ethoxylate.

After curing overnight at room temperature, the time for the drop of water to solubilize the coating is measured. As the amount of cross-linker is increased, the time for solubilizing the coating is increased.

Samples are also prepared, as described above, except the coating is exposed to a secondary cure by heating for about 30 minutes at a temperature of about 80° C. After the secondary cure, the time for solubilizing the coating is increased.

What is claimed is:

1. A grafted polymer comprising:
   i. a first component including a polymer formed by polymerizing the alkene groups of one or more monomers including a 1,1-diester-1-alkene compound, attached to;
   ii. a second component that is a hydrophilic component, wherein the hydrophilic component includes a cation or a water-soluble polymer;
   wherein the grafted polymer has a network structure.

2. The grafted polymer of claim 1, wherein the polymer of the first component has a first end and a second end and a backbone connecting the first and a second ends, the backbone including about 92 atomic percent or more carbon atoms.

3. The grafted polymer of claim 1, wherein the hydrophilic component is a water-soluble polymer selected from the group consisting of a polyacrylamide, a polyvinyl alcohol, a polyacrylic acid, a polyalkoxide, a water soluble amine containing polymer, a polyethyleneimine, a polymer including quaternary ammonium compounds, a copolymer of vinyl methyl ether and maleic anhydride, polyvinylpyrrolidone, or any combination thereof.

4. The grafted polymer of claim 1, wherein the second, component includes: i) a quaternary ammonium compound;

or ii) a polyalkoxide wherein the polyalkoxide includes 65 weight percent or more ethylene oxide groups, based on the total weight of the polyalkoxide.

5. A grafted polymer comprising:
i. a first component including a polymer formed by polymerizing the alkene groups of one or more monomers including a 1,1-diester-1-alkene compound, attached to;
ii. a second component that is a hydrophilic component, wherein the hydrophilic component includes a cation or a water-soluble polymer;
wherein the one or more monomers includes a multifunctional 1,1-disubstituted-1-alkene monomer having two or more polymerizable alkene groups.

6. The grafted polymer of claim 1, wherein the grafted polymer is characterized by one or any combination of the following:
i) about 20 atomic percent or more of the monomers of the first component are directly attached to the second component; or
ii) the first component is present in an amount of about 10 weight percent or more based on the total weight of the graft polymer; or
iii) the second component is present in an amount of about 20 weight percent or more based on the total weight of the graft polymer; or
iv) the total amount of the first component and the second component is about 50 weight percent or more based on the total weight of the graft polymer.

7. The grafted polymer of claim 1, wherein about 10 atomic percent or more of the monomers of the first component are 1,1-diester-1-alkenes that are free of direct attachment to the hydrophilic component.

8. The grafted polymer of claim 1, wherein:
i) the grafted polymer consists essentially of the first component consisting only of one or more 1,1-diester-1-alkene compounds, and the second component consisting only of the water-soluble polymer or the cation; and/or
ii) the grafted polymer is associated with an anion that includes a sulfonate ion or a sulfate ion.

9. The grafted polymer of claim 1, wherein the 1,1-diester-1-alkene compound includes one or more 1,1-diester-1-alkenes having a structure:

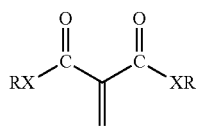

wherein R is a hydrocarbyl group which may contain one or more heteroatoms and X is oxygen.

10. The grafted polymer of claim 1, wherein the 1,1-diester-1-alkene compound is a methylene malonate having a structure:

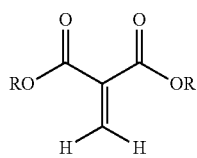

wherein R is separately in each occurrence alkyl, alkenyl, $C_{3-9}$ cycloalkyl, heterocyclyl, alkyl heterocyclyl, aryl, aralkyl, alkaryl, heteroaryl, or polyoxyalkylene, or both of the R's form a 5-7 membered cyclic or heterocyclic ring.

11. The grafted polymer of claim 1, wherein the grafted polymer includes about 30 to about 95 weight percent of the water-soluble polymer, based on the total weight of the grafted polymer.

12. The grafted polymer of claim 5, wherein the polymer of the first component has a first end and a second end and a backbone connecting the first and a second ends, the backbone including about 92 atomic percent or more carbon atoms, based on the total atomic percent.

13. The grafted polymer of claim 5, wherein the hydrophilic component is a water-soluble polymer selected from the group consisting of a polyacrylamide, a polyvinyl alcohol, a polyacrylic acid, a polyalkoxide, a water soluble amine containing polymer, a polyethyleneimine, a polymer including quaternary ammonium compounds, a copolymer of vinyl methyl ether and maleic anhydride, polyvinylpyrrolidone, or any combination thereof.

14. The grafted polymer of claim 5, wherein the second component includes: i) a quaternary ammonium compound; or ii) a polyalkoxide wherein the polyalkoxide includes 65 weight percent or more ethylene oxide groups, based on the total weight of the polyalkoxide.

15. The grafted polymer of claim 5, wherein the grafted polymer is characterized by one or any combination of the following:
i) about 20 atomic percent or more of the monomers of the first component e directly attached to the second component; or
ii) the first component is present in an amount of about 10 weight percent or more based on the total weight of the graft polymer; or
iii) the second component is present in an amount of about 20 weight percent or more based on the total weight of the graft polymer; or
iv) the total amount of the first component and the second component is about 50 weight percent or more based on the total weight of the graft polymer.

16. The grafted polymer of claim 5, wherein about 10 atomic percent or more of the monomers of the first component are 1,1-diester-1-alkenes that are free of direct attachment to the hydrophilic component.

17. The grafted polymer of claim 5, wherein:
i) the grafted polymer consists essentially of the first component consisting only of one or more 1,1-diester-1-alkene compounds, and the second component consisting only of the water-soluble polymer or the cation; and/or
ii) the grafted polymer is associated with an anion that includes a sulfonate ion or a sulfate ion.

18. The grafted polymer of claim 5, wherein the 1,1-diester-1-alkene compound includes one or more 1,1-diester-1-alkenes having a structure:

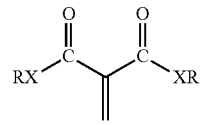

wherein R is a hydrocarbyl group which may contain one or more heteroatoms and X is oxygen.

19. The grafted polymer of claim 5, wherein the 1,1-diester-1-alkene compound is a methylene malonate having a structure:

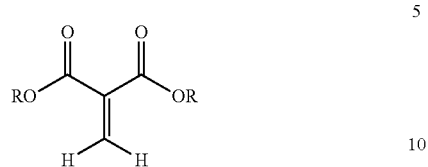

wherein R is separately in each occurrence alkyl, alkenyl, $C_{3-9}$ cycloalkyl, heterocyclyl, alkyl heterocyclyl, aryl, aralkyl, alkaryl, heteroaryl, or polyoxyalkylene, or both of the R's form a 5-7 membered cyclic or heterocyclic ring.

20. The grafted polymer of claim 5, wherein the grafted polymer includes about 30 to about 95 weight percent of the water-soluble polymer, based on the total weight of the grafted polymer.

\* \* \* \* \*